(12) United States Patent
Komukai et al.

(10) Patent No.: US 8,573,824 B2
(45) Date of Patent: Nov. 5, 2013

(54) ILLUMINATION OPTICAL UNIT FOR ENDOSCOPE AND METHOD OF MANUFACTURING THE SAME

(75) Inventors: Makito Komukai, Kanagawa (JP); Akira Mizuyoshi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 168 days.

(21) Appl. No.: 13/304,152

(22) Filed: Nov. 23, 2011

(65) Prior Publication Data

US 2012/0136212 A1 May 31, 2012

(30) Foreign Application Priority Data

Nov. 30, 2010 (JP) ................................ P2010-267038

(51) Int. Cl.
*F21V 5/00* (2006.01)
(52) U.S. Cl.
USPC ........... 362/574; 362/572; 362/551; 362/231; 362/581; 600/160; 600/178; 600/476
(58) Field of Classification Search
USPC .......... 362/572, 574, 551, 231, 581; 600/160, 600/178, 476
See application file for complete search history.

(56) References Cited

U.S. PATENT DOCUMENTS

| 5,334,191 | A  | * | 8/1994 | Poppas et al. | 606/12 |
| 6,070,096 | A  | * | 5/2000 | Hayashi | 600/477 |
| 2002/0177751 | A1 | * | 11/2002 | Ueno et al. | 600/160 |
| 2008/0039695 | A1 | * | 2/2008 | Takaoka et al. | 600/178 |
| 2008/0112182 | A1 |   | 5/2008 | Kazakevich | |
| 2010/0172148 | A1 | * | 7/2010 | Komazaki et al. | 362/551 |

FOREIGN PATENT DOCUMENTS

| EP | 1 787 571 A1 | 5/2007 |
| JP | 2007-020937 A | 2/2007 |
| WO | WO 2008/082928 A1 | 7/2008 |

* cited by examiner

*Primary Examiner* — Ali Alavi
(74) *Attorney, Agent, or Firm* — Birch, Stewart, Kolasch & Birch, LLP (57) ABSTRACT

The periphery of a fluorescent body is reliably sealed, and entry of moisture or volatilized gas is prevented. An illumination optical unit includes an optical fiber, a fluorescent body, a ferrule as a holding member holding the fluorescent body and the optical fiber, a tubular sleeve member that covers the outer periphery of the fluorescent body, and a protective cover. The ferrule holds the fluorescent body and is fitted into a fitting hole of the sleeve member. An inner peripheral face of the sleeve member and an outer peripheral face of the protective cover are bonded together to seal the distal end side of the fluorescent body, and the fitting hole of the sleeve member and an outer peripheral face of the ferrule are bonded together to bond the proximal end side of the fluorescent body.

14 Claims, 10 Drawing Sheets

ILLUMINATION OPTICAL UNIT FOR ENDOSCOPE AND METHOD OF MANUFACTURING THE SAME

BACKGROUND OF THE INVENTION

1. Field of the Invention

The present invention relates to an illumination optical unit for an endoscope that radiates a part to be observed in a subject with illumination light in order to observe the inside of the subject, and a method of manufacturing the same.

2. Description of the Related Art

In the related art, diagnosis using an endoscope is widely prevalent in the medical field. The endoscope includes, at the distal end of an insertion part to be inserted into a subject, an observation window for incorporating image light of the subject and an illumination window for radiating illumination light toward the subject. The endoscope is connected to a light source device via a cord or a connector.

The light source device has a light source for supplying the illumination light for illuminating the inside of the subject to the endoscope. The illumination light from the light source is guided to the distal end of the insertion part by a light guide inserted through the endoscope. In the related art, a white light source, such as a xenon lamp or a halogen lamp, has been used as the light source that constitutes the light source device. However, a light source device using a laser beam source has recently began to be used instead of this white light source.

An endoscope in which a laser beam supplied from the light source device using this laser beam source is guided to the distal end of the insertion part by the light guide, and a fluorescent body arranged on the distal side end of the light guide is excited by the laser beam to emit light so as to radiate a body cavity with white illumination light is described in JP2007-20937A. In the endoscope described in JP2007-20937A, the fluorescent body is provided integrally with a cover glass, the distal end portion of the insertion part is formed with a through hole to which the light guide and the cover glass are attached, and the fluorescent body attached to the distal end portion of the insertion part along with the cover glass is arranged at the emission end of the light guide.

Additionally, the endoscope is required to radiate a higher intensity of illumination light. Therefore, a reflective film with high reflectivity may be provided around the fluorescent body in order to efficiently use the excited and emitted light as the illumination light. As this reflective film with high reflectivity, it is known that a metal film of silver, aluminum, or the like is suitable.

SUMMARY OF THE INVENTION

When diagnosis is performed using an endoscope, the inside of the endoscope insertion part to be inserted into a body cavity is brought into a high-humidity state, and grease containing molybdenum disulfide is applied to the outer peripheral face of the insertion part as a lubricant. Moreover, the endoscope is subjected to the washing disinfection processing of dipping the endoscope in a disinfectant including peracetic acid or the like after the end of diagnosis. As such, since moisture, grease, and medicine such as a disinfectant is apt to enter the inside of the insertion part. Thus, in order to prevent deterioration of the fluorescent body or the reflective film that is vulnerable to moisture or medicine, a structure that seals the periphery of the fluorescent body or the reflective film is desired.

As described in the above JP2007-20937A, when the fluorescent body is arranged inside the through hole formed in the distal end portion of the insertion part, moisture or gas volatilized from medicine may enter the inside of the insertion part, and may come into contact with the fluorescent body. However, JP2007-20937A does not disclose or suggest sealing the periphery of the fluorescent body at all.

The present invention has been made in view of the above-mentioned problems and an object of the present invention is to provide to reliably seal the periphery of a fluorescent body, and prevent entry of moisture or volatilized gas.

An illumination optical unit for an endoscope of the present invention is an illumination optical unit for an endoscope including: an optical fiber that guides a laser beam supplied from a laser beam source to the distal end of the optical fiber and emits the guided laser beam from the distal end; a fluorescent body that is excited by the laser beam emitted from the optical fiber to emit florescent light and that forms white light including the fluorescent light and the laser beam; a holding member that holds the fluorescent body, has a fluorescent body holding portion opened on the distal end side, and a through hole that is continuous from the proximal end of the fluorescent body holding portion and allows the optical fiber to be inserted therethrough, and is formed in a substantially cylindrical shape; a sleeve member that has an inner peripheral face fitted to an outer peripheral face of the holding member and has the distal end and the proximal end opened; and a protective cover that is held by the sleeve member, covers the distal end side of the fluorescent body, and transmits the fluorescent light and the laser beam. Here, the optical fiber is made to protrude from the proximal ends of the holding member and the sleeve member, the distal end side of the fluorescent body is sealed by bonding the sleeve member and the protective cover, and the proximal end side of the fluorescent body is sealed by bonding the sleeve member and the holding member.

Preferably, the illumination optical unit for an endoscope further includes a protective tube that covers the optical fiber. The sleeve member includes a first sleeve member that holds the protective cover and is located on the distal end side, and a second sleeve member combined with the proximal end side of the first sleeve member, and the protective tube is fixed to an outer peripheral face of the second sleeve member.

Preferably, the first and second sleeve members are formed with an outer peripheral end that is continuous from one of the mutually facing end faces and an inner peripheral end that is continuous from the other end face, and the outer peripheral end and the inner peripheral end fit to each other.

Preferably, the surface of the fluorescent body holding portion of the holding member is provided with a reflective film that reflects the white light emitted from the fluorescent body. Additionally, preferably, wherein an adhesive that bonds the sleeve member and the protective cover is a silicon-based adhesive.

A method of manufacturing an illumination optical unit for an endoscope of the present invention is a method of manufacturing an illumination optical unit for an endoscope including: an optical fiber that guides a laser beam supplied from a laser beam source to the distal end of the optical fiber and emits the guided laser beam from the distal end; a fluorescent body that is excited by the laser beam emitted from the optical fiber to emit florescent light and that forms white light including the fluorescent light and the laser beam; a holding member that holds the fluorescent body, has a fluorescent body holding portion opened on the distal end side, and a through hole that is continuous from the proximal end of the fluorescent body holding portion and allows the optical fiber to be inserted therethrough, and is formed in a substantially cylindrical shape; a sleeve member that has an inner peripheral face fitted to an outer peripheral face of the holding member and has the distal end and the proximal end opened; and a protective cover that is held by the sleeve member, covers the distal end side of the fluorescent body, and transmits the fluorescent light and the laser beam. The method includes: bonding the sleeve member and the protective cover to seal the distal end side of the fluorescent body; inserting the holding member holding the fluorescent body and the optical fiber into the inside of the sleeve member from the proximal end side of the sleeve member whose distal end is sealed with the protective cover, to bring the fluorescent body into close contact with the protective cover; and bonding the holding member and the sleeve member together to seal the proximal end side of the fluorescent body, in a state where the fluorescent body is brought into close contact with the protective cover, and the optical fiber is arranged on the proximal end side of the fluorescent body.

According to the present invention, the outer peripheral face of the holding member holding the optical fiber and the fluorescent body fits to the inner peripheral face of the sleeve member, the optical fiber is made to protrude from the proximal ends of the holding member and the sleeve member, the sleeve member and the protective cover are bonded together to seal the distal end side of the fluorescent body, and the sleeve member and the holding member are bonded to seal the proximal end side of the fluorescent body. Thus, it is possible to reliably seal the periphery of the fluorescent body, and to prevent entry of moisture or volatilized gas.

DESCRIPTION OF THE PREFERRED EMBODIMENTS

Figure 1:
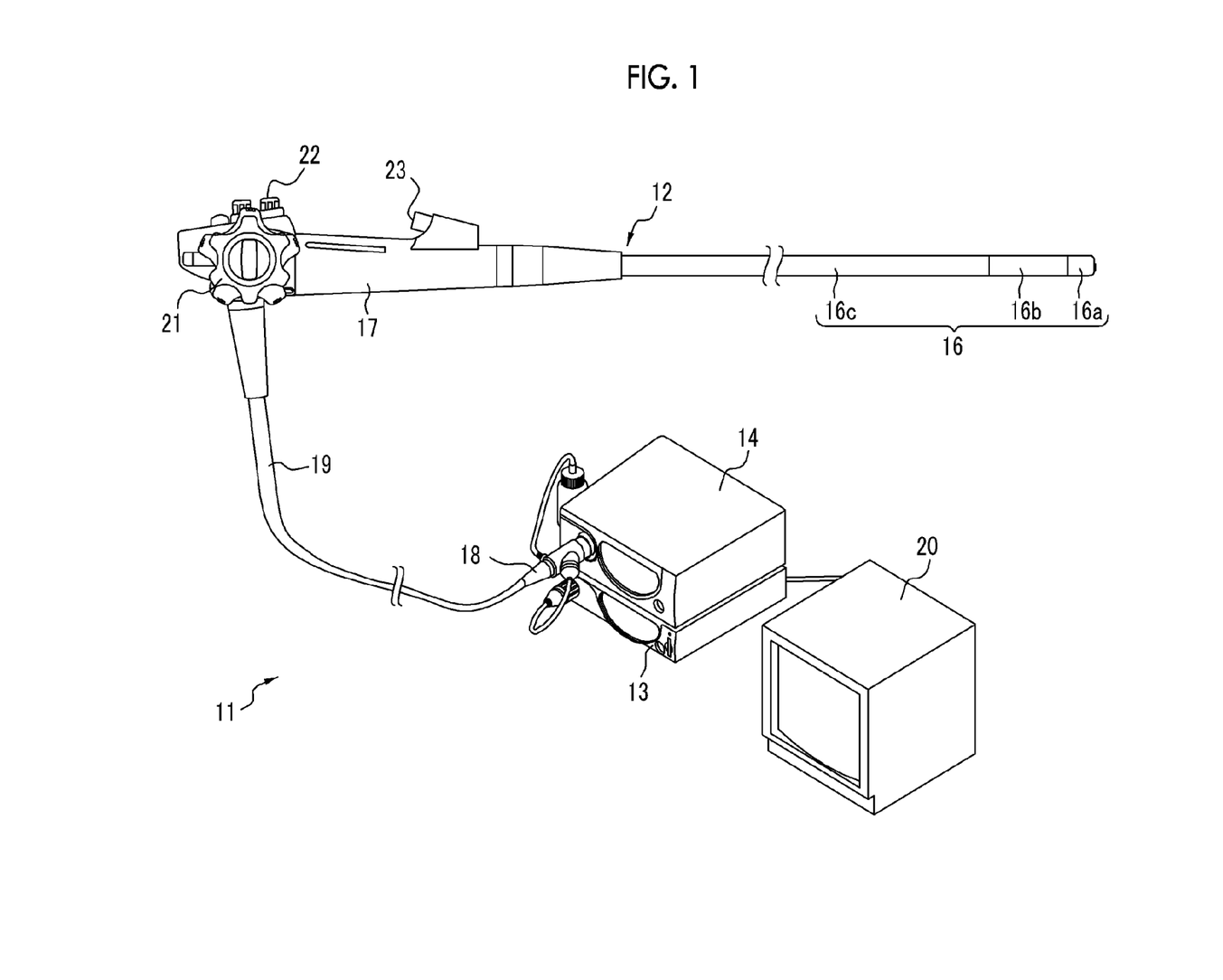
FIG. 1 is an outline view showing the configuration of an electronic endoscope system.

As shown in FIG. 1, an electronic endoscope system 11 includes an electronic endoscope 12, a processor device 13, and a light source device 14. The electronic endoscope 12 has a flexible insertion part 16 to be inserted into the body of a subject, a manipulating part 17 connected to the proximal end portion of the insertion part 16, a connector 18 connected to the processor device 13 and the light source device 14, and a universal cord 19 connecting the manipulation part 17 and the connector 18 together.

The insertion part 16 includes a distal end portion 16a provided at the distal end thereof and having a CCD type image sensor 33 (refer to FIG. 4, hereinafter referred to as CCD) for radiographing the inside of a subject built therein, a bendable bending portion 16b connected to the proximal end of the distal end portion 16a, and a flexible tube portion 16c connected to the proximal end of the bending portion 16b and having flexibility.

The manipulating part 17 is provided with manipulating members, such as an angle knob 21 for bending the bending portion 16b vertically and horizontally, and air supply and water supply buttons 22 for jetting air and water from the distal end portion 16a. Additionally, the manipulating part 17 is provided with a forceps opening 23 for allowing treatment tools, such as an electric scalpel, to be inserted into a forceps channel (not shown).

The processor device 13 is electrically connected to the light source device 14, and controls the operation of the electronic endoscope system 11 in general. The processor device 13 supplies electric power to the electronic endoscope 12 via a transmission cable inserted through the universal cord 19 or the insertion part 16, and controls the driving of the CCD 33. Additionally, the processor device 13 acquires an imaging signal output from the CCD 33 via the transmission cable, and performs various image processing to generate image data. The image data generated by the processor device 13 is displayed as an observation image on a monitor 20 cable-connected to the processor device 13.

Figure 2:
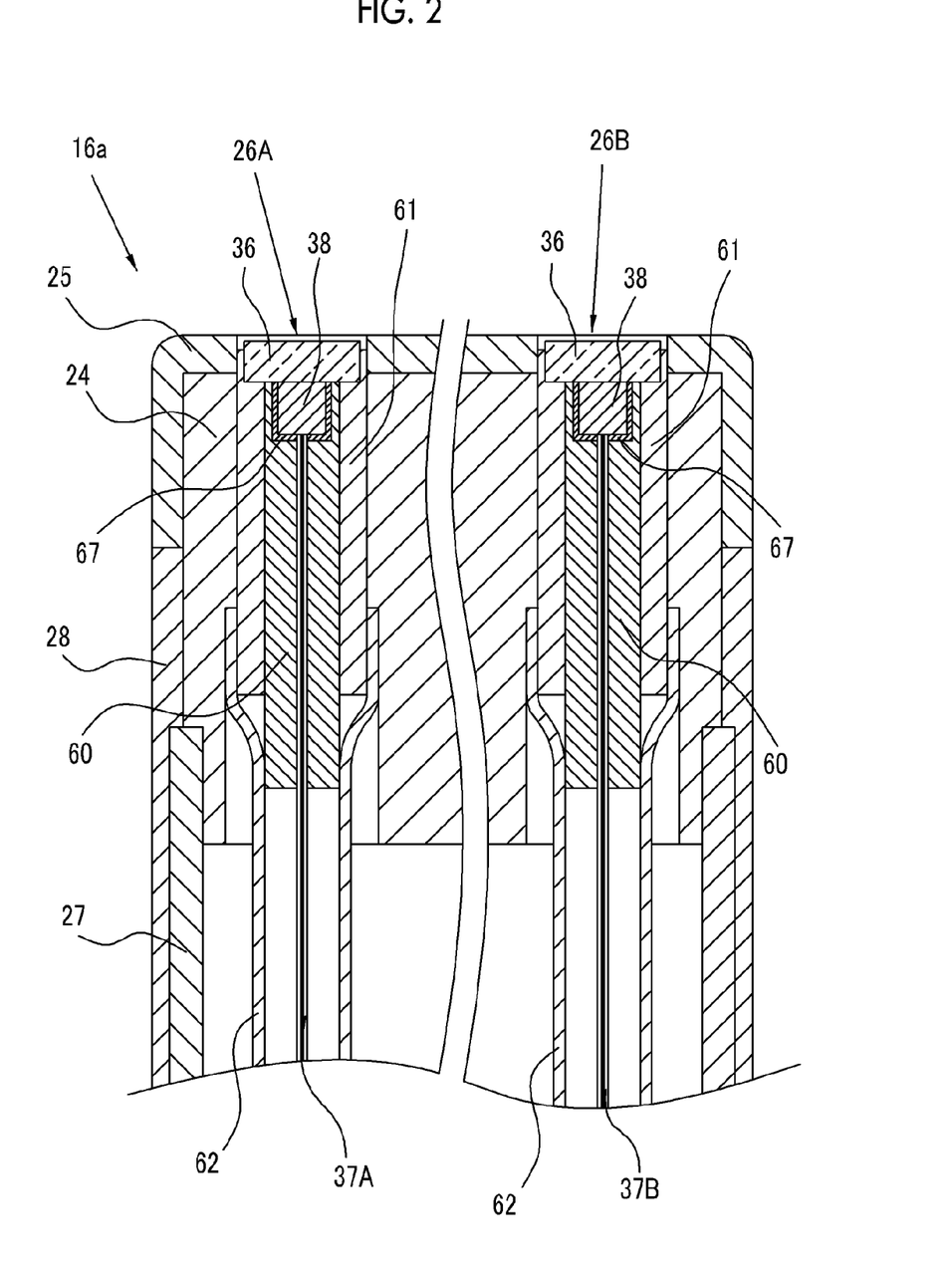
FIG. 2 is a cross-sectional view of essential portions showing the configuration of the distal end portion of an electronic endoscope.

As shown in FIG. 2, the distal end portion 16a includes a distal end hard section 24, and a distal end protection cap 25 mounted on the distal end side of the distal end hard section 24. The distal end hard section 24 is made of metal, such as stainless steel, and has a plurality of through holes formed along the longitudinal direction thereof. Various parts, such as an imaging optical system 32 (refer to FIG. 4), the CCD 33, illumination optical units 26A and 26B, the forceps channel, the air supply and water supply channels (not shown), are attached to the respective through holes of the distal end hard section 24. A rear end of the distal end hard section 24 is coupled to a bending piece 27 at the distal end that constitutes the bending portion 16b. Additionally, the outer periphery of the distal end hard section 24 is covered with a jacket tube 28.

Figure 3:
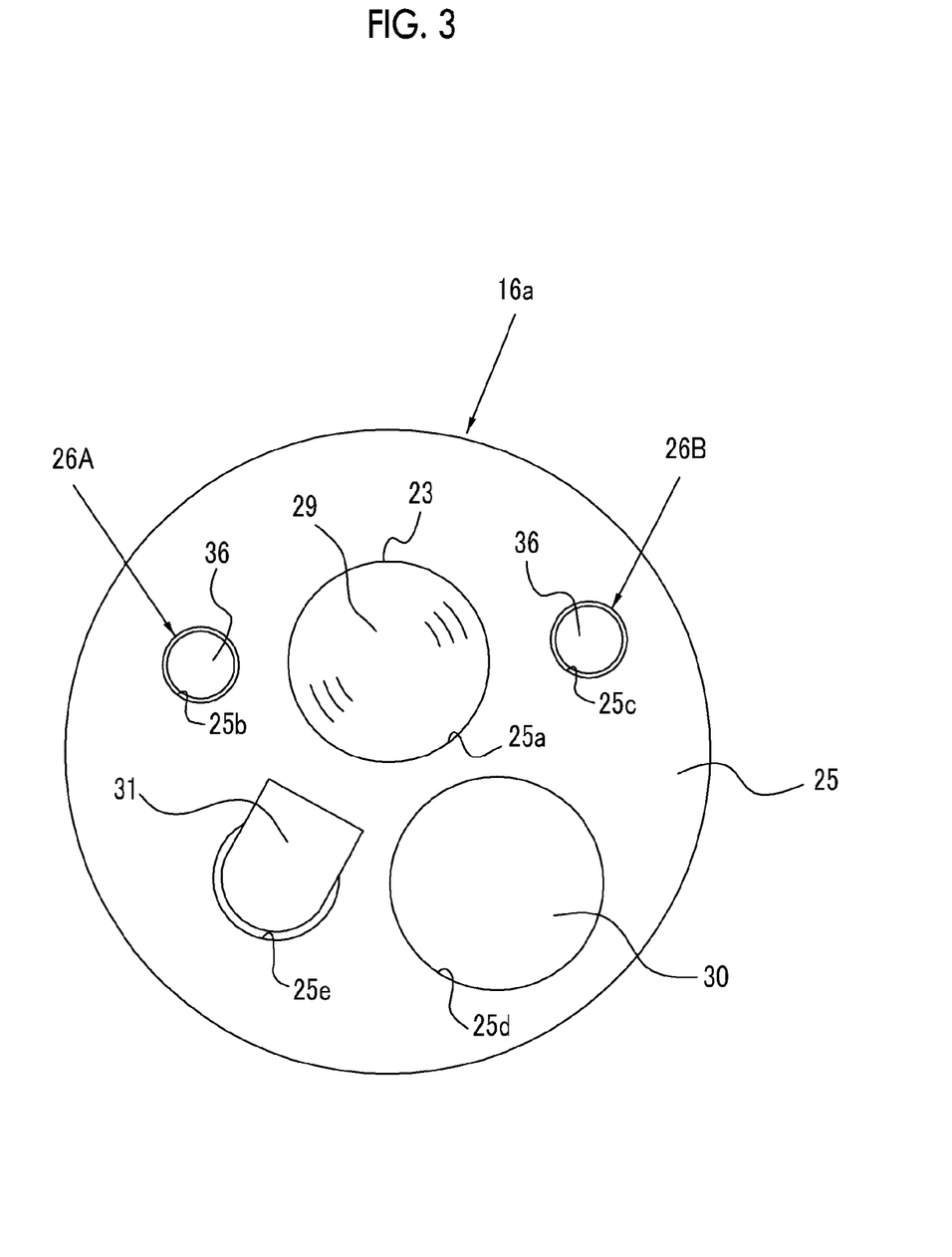
FIG. 3 is a plan view of the distal end portion of the electronic endoscope.

The distal end protection cap 25 is made of rubber or resin, and is formed with through holes at positions corresponding to the various parts held by the distal end hard section 24. As shown in FIG. 3, the distal end protection cap 25 exposes an observation window 29, the illumination optical units 26A and 26B, a forceps outlet 30, and an air supply and water supply nozzle 31, and the like from through holes 25a to 25e. A pair of illumination optical units 26A and 26B is disposed at positions symmetrical to each other across the observation window 29.

Figure 4:
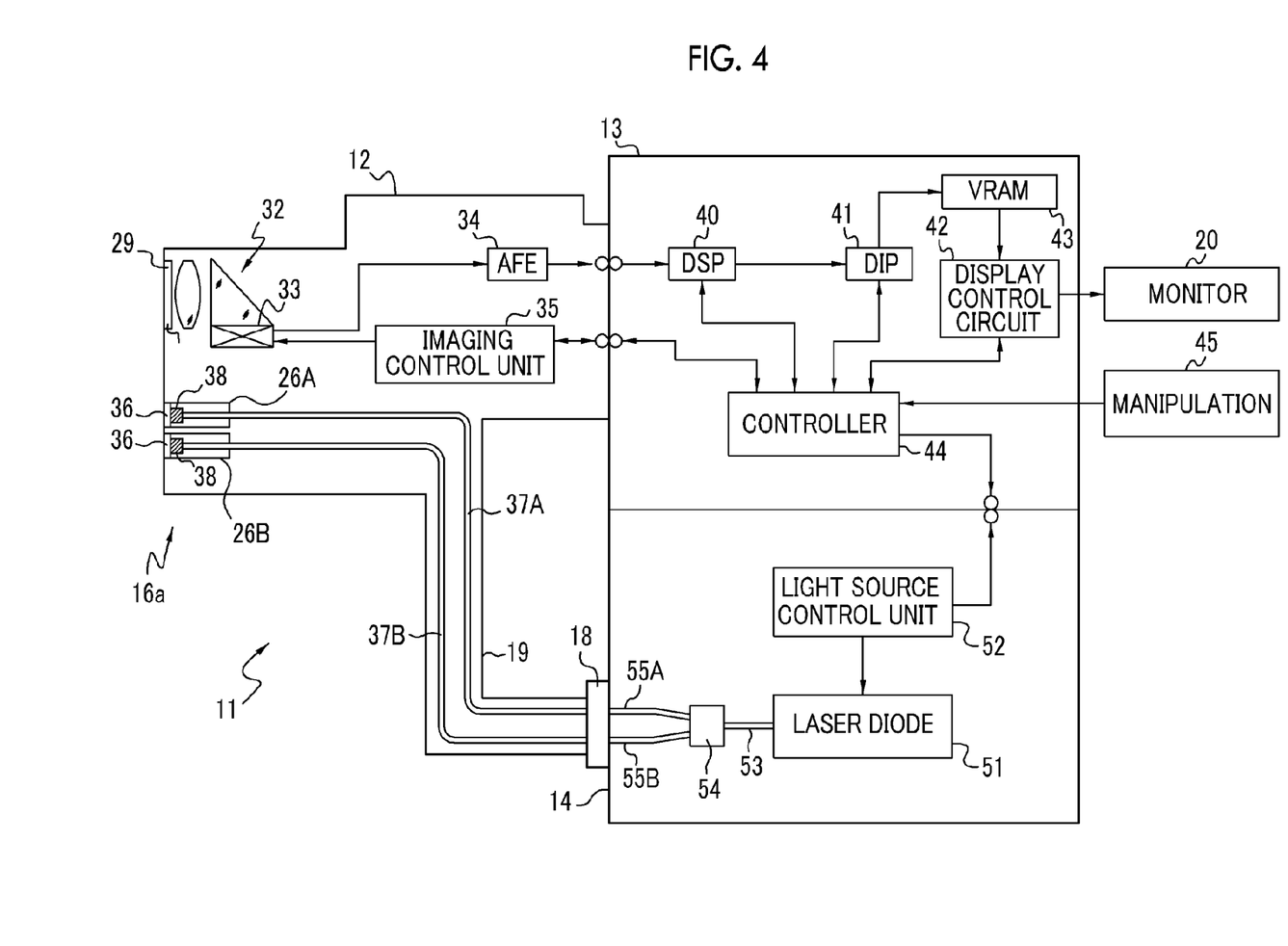
FIG. 4 is a block diagram showing an electrical configuration of the electronic endoscope system.

As shown in FIG. 4, the CCD 33 is arranged in an inner part of the observation window 29 inside the distal end portion 16a such that an image in a subject is focused on an imaging surface by the imaging optical system 32 including a lens group and a prism.

The CCD 33 performs photoelectric conversion of the image in the subject focused on the imaging plane by the imaging optical system 32 to accumulate signal charges, and outputs the accumulated signal charges as imaging signals. The output imaging signals are sent to an AFE 34. The AFE 34 is constituted by a correlated double sampling (CDS) circuit, an automatic gain control (AGC) circuit, an A/D converter (all of these are not shown), and the like. The CDS performs correlation double sampling processing on the imaging signals output from the CCD 33, and removes the noise generated by driving the CCD 33. The AGC amplifies the imaging signals whose noise is removed by the CDS.

The imaging control unit 35 is connected to a controller 44 in the processor device 13 when the electronic endoscope 12 and the processor device 13 are connected together, and sends a driving signal to the CCD 33 when an instruction is issued from the controller 44. The CCD 33 outputs the imaging signals to the AFE 34 at a predetermined frame rate on the basis of the driving signal from the imaging control unit 35.

The illumination optical units 26A and 26B are units that radiate illumination light into a subject. The distal end side of the illumination optical units 26A and 26B is sealed by a protective cover 36, and is exposed from the distal end face of the distal end portion 16a, that is, the through holes 25b and 25c of the distal end protection cap 25, as an illumination window.

Optical fibers 37A and 37B that constitute the illumination optical units 26A and 26B guide a blue laser beam supplied from the light source device 14, and emit the laser beam to the fluorescent body 38 provided on the emission end side. Hereinafter, the emission end side of the optical fibers 37A and 37B is referred to as "distal end side", and the incident end side of the optical fibers 37A and 37B is referred to as "proximal end side". The fluorescent body 38 is made of, for example, YAG or BAM ($BaMgAl_{10}O_{17}$), absorbs portions of the blue laser beam emitted from the optical fibers 37A and 37B and is excited to emit green to yellow light beams. For this reason, in the illumination optical units 26A and 26B, a blue light beam transmitted through the fluorescent body 38 while being diffused in the fluorescent body and the green to yellow fluorescent light beams excited and emitted from the fluorescent body 38 are combined together to form white (pseudo-white) illumination light. The irradiation range of the illumination light is approximately equal to or greater than a radiographing range using the electronic endoscope 12, and the illumination light is almost uniformly radiated to the entire surface of an observation image.

The processor device 13 includes a digital signal processing circuit (DSP) 40, a digital image processing circuit (DIP) 41, a display control circuit 42, a VRAM 43, a controller 44, a manipulation unit 45, and the like.

The controller 44 controls the operation of the overall processor device 13 in general. The DSP 40 performs various signal processing, such as color separation, color interpolation, gain compensation, white balance adjustment, and gamma compensation, on the imaging signals output from the AFE 34 of the electronic endoscope 12, and generates image data. The image data generated by the DSP 40 is input to a working memory of a DIP 41. Additionally, the DSP 40 generates ALC control data required for the automatic control (ALC control) of, for example, the quantity of illumination light, such as an average luminance value obtained by averaging the luminance of respective pixels of the image data generated, and inputs the ALC control data to the controller 44.

The DIP 41 performs various image processing, such as electronic variable magnification, color enhancement processing, and edge enhancement processing, on the image data generated by the DSP 40. The image data subjected the various image processing by the DIP 41 is temporarily stored in a VRAM 43 as an observation image, and input to the display control circuit 42. The display control circuit 42 selects and acquires the observation image from the VRAM 43, and displays the observation image on the monitor 20.

The manipulation unit 45 includes well-known input devices, such as a control panel, a mouse, and a keyboard that are provided in the housing of the processor device 13. The controller 44 operates respective parts of the electronic endoscope system 11 according to a manipulation signal from the manipulation unit 45 or the manipulating part 17 of the electronic endoscope 12.

The light source device 14 includes a laser diode (LD) 51 and a light source control unit 52 as a laser beam source. The LD 51 is a light source that emits a blue laser beam with a central wavelength of 445 nm and that guides the laser beam to an optical fiber 53 via a condensing lens (not shown). The optical fiber 53 is connected to two optical fibers 55A and 55B via a branch coupler 54. The optical fibers 55A and 55B are connected to the optical fibers 37A and 37B of the electronic endoscope 12 via a connector 18. For this reason, a blue laser beam emitted from LD 51 is incident on the fluorescent body 38 that constitutes the illumination optical units 26A and 26B. Then, due to the blue laser light being made incident, the green to yellow fluorescent light beams excited and emitted from the fluorescent body 38 are combined therewith and radiated into a subject as white (pseudo-white) illumination light.

The light source control unit 52 adjusts the timing of turning-on and turning-off of the LD 51 according to an adjustment signal or synchronization signal input from the controller 44 of the processor device 13. Moreover, the light source control unit 52 communicates with the controller 44 and adjusts the quantity of light emission of the LD 51, thereby adjusting the quantity of the illumination light radiated into a subject. The control of the quantity of illumination light by the light source control unit 52 is ALC (Auto Light Control) control that adjusts the quantity of illumination light automatically according to the luminance of the radiographed observation image or the like, and is performed on the basis of the ALC control data generated by the DSP 40.

Figure 5:
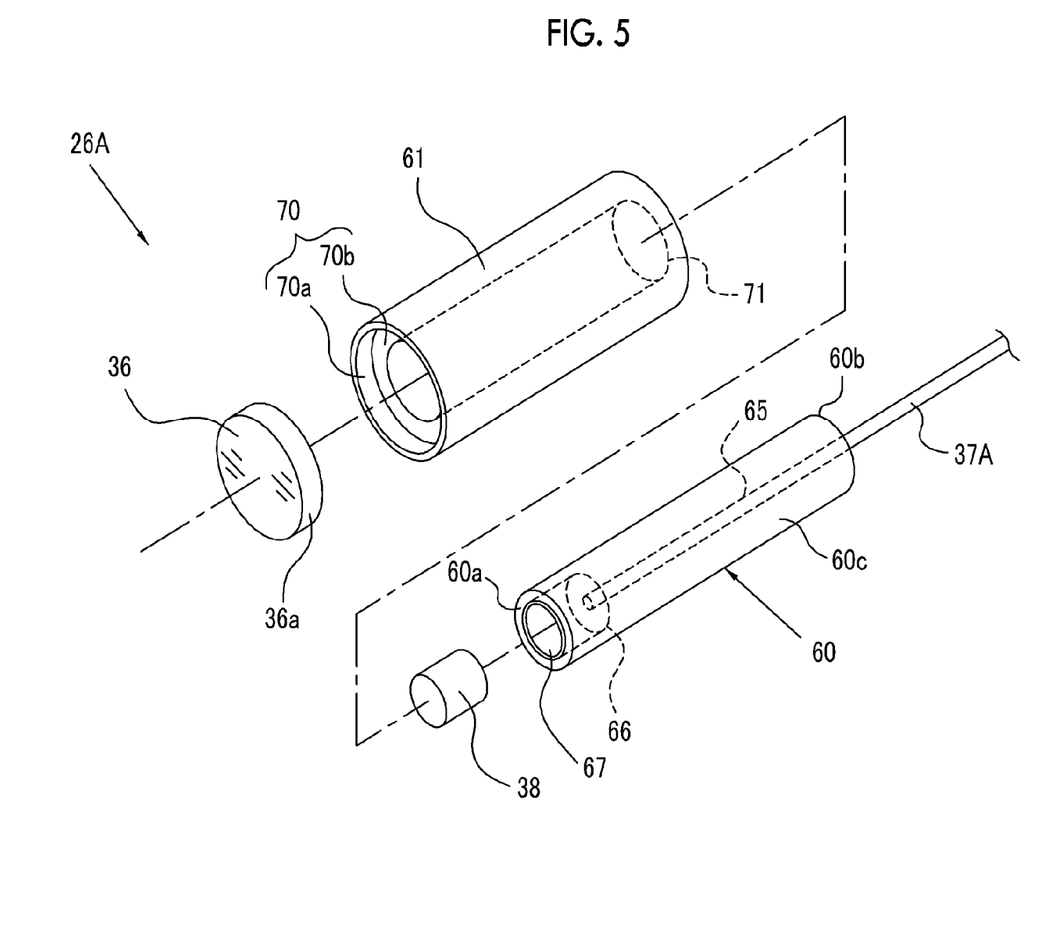
FIG. 5 is an exploded perspective view showing the configuration of an illumination optical unit.

As shown in FIGS. 2 and 5, the illumination optical unit 26A includes the optical fiber 37A, the fluorescent body 38, a ferrule 60 as a holding member holding the fluorescent body 38 and the optical fiber 37A, a tubular sleeve member 61 that covers the outer periphery of the fluorescent body 38, and the protective cover 36, and the distal end side and proximal end side of the fluorescent body 38 are sealed as will be described below. Additionally, the illumination optical unit 26B includes the optical fiber 37B, the fluorescent body 38, the ferrule 60, the sleeve member 61, and the protective cover 36, and similarly to the illumination optical unit 26A, has a configuration in which the ferrule 60 holds the fluorescent body 38 and the optical fiber 37B, and the sleeve member 61 covers the outer periphery of the fluorescent body 38, and seals the distal end side and proximal end side of the fluorescent body 38. Moreover, outer peripheral faces of the optical fibers 37A and 37B are covered with a protective tube 62 (refer to FIG. 2). The protective tube 62 has the distal end portion fixed to the outer peripheral face of the sleeve member 61, and is inserted through the insertion part 16, the manipulation unit 17, and the universal cord 19 along with the optical fibers 37A and 37B. In addition, as the optical fibers 37A and 37B, it is preferable to use a single mode fiber with a diameter of about 300 μm.

The ferrule 60 is formed in a substantially cylindrical shape, and has an insertion hole 65 through which the optical fiber 37A is inserted. A fluorescent body holding portion 66 that holds the fluorescent body 38 is formed continuously from a distal end face 60a of the ferrule 60. The fluorescent body holding portion 66 becomes concave from the distal end face 60a in conformity with the appearance of the fluorescent body 38, and is formed in the shape of a recess that is opened on the distal end side that faces the protective cover 36. The insertion hole 65 is continuous with the proximal end of the fluorescent body holding portion 66. The insertion hole 65 and the optical fiber 37A are fitted to each other by making the gap therebetween small.

The surface of the fluorescent body holding portion 66 is provided with a reflective film 67. The reflective film 67 is made of a metal film, such as silver or aluminum, and is formed in the shape of a thin film, for example, by plating, vapor deposition, sputtering, or the like. The fluorescent body 38 is held inside the fluorescent body holding portion 66 in contact with the reflective film 67. The illumination light emitted from the fluorescent body 38 can be reflected by the reflective film 67 and efficiently used. When the fluorescent body 38 is held by the fluorescent body holding portion 66, the distal end faces of the fluorescent body 38 and the reflective film 67 are formed so as to be same level with the distal end face 60a of the ferrule 60. The insertion hole 65 is formed along the central axis of the ferrule 60. The distal end portion of the optical fiber 37A fits into the insertion hole 65, and is held behind the fluorescent body 38. In the ferrule 60, the fluorescent body 38 is held in the fluorescent body holding portion 66 and the optical fiber 37A is held in the insertion hole 65, and an outer peripheral face 60c is fitted to the sleeve member 61 in a state where the optical fiber 37 protrudes from the proximal end face 60b.

The sleeve member 61 is formed in a substantially cylindrical shape that has a receiving portion 70 that receives the protective cover 36, and a fitting hole 71 into which the outer peripheral face 60c of the ferrule 60 fits, sequentially from the distal end side. The receiving portion 70 is formed so as to have a larger internal diameter than that of the fitting hole 71. The receiving portion 70 has an inner peripheral face 70a that faces an outer peripheral face 36a of the protective cover 36, and a bottom face 70b that intersects the inner peripheral face 70a and faces the proximal end face 36b of the protective cover 36. The fitting hole 71 is continuous up to the proximal end face of the sleeve member 61 along the center of the sleeve member 61 from the bottom face 70b.

The protective cover 36 is formed substantially in the shape of a disc from a material through which the illumination light (white light) emitted from the fluorescent body 38, that is, the blue light beam transmitted through the fluorescent body 38 while being diffused in the fluorescent body and the green to yellow fluorescent light beams excited and emitted from the fluorescent body 38 can be transmitted. The protective cover 36 is formed from, for example, quartz glass, sapphire glass, or the like.

Figure 6:
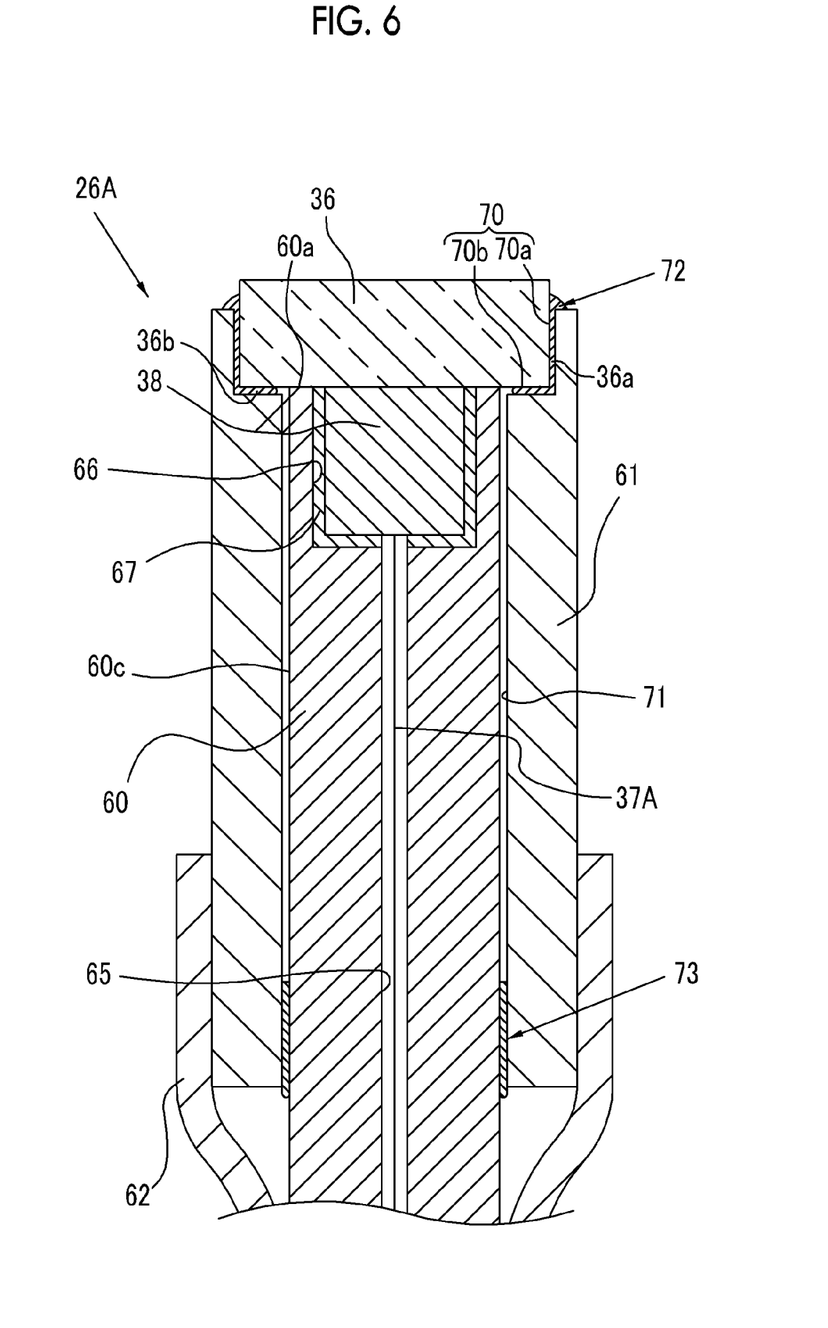
FIG. 6 is a cross-sectional view of essential parts showing a configuration around the fluorescent body.

As shown in FIG. 6, in the sleeve member 61, the distal end side of the fluorescent body 38 is sealed as the protective cover 36 is bonded to the receiving portion 70, and the proximal end side of the fluorescent body 38 is sealed as the outer peripheral face 60c of the ferrule 60 is bonded to the fitting hole 71.

When the protective cover 36 is bonded to the receiving portion 70 in order to seal the distal end side of the fluorescent body 38, an adhesive 72 is poured into a gap between the receiving portion 70 and the protective cover 36, that is, between the inner peripheral face 70a of the receiving portion 70 and the outer peripheral face 36a of the protective cover 36. As the adhesive 72, for example, a silicon-based adhesive is used. Additionally, when the viscosity of the adhesive 72 is low, glass beads may be mixed into the adhesive 72.

In order to seal the proximal end side of the fluorescent body 38, when the outer peripheral face 60c of the ferrule 60 is bonded to the fitting hole 71, an adhesive 73 is poured between the fitting hole 71 and the outer peripheral face 60c of the ferrule 60. As the adhesive 73, the same adhesive as the adhesive 72 is used. Additionally, when the viscosity of the adhesive 73 is low, glass beads may be mixed similarly to the adhesive 72.

In a manufacturing process of manufacturing the illumination optical unit 26A of the above configuration, first, a first bonding step of bonding of the protective cover 36 to the receiving portion 70 is performed in order to seal the distal end side of the fluorescent body 38. In this first bonding step, a predetermined amount of the adhesive 72 is poured into and solidified between the inner peripheral face 70a of the receiving portion 70 and the outer peripheral face 36a of the protective cover 36. After this first bonding step, the ferrule 60 that holds the fluorescent body 38 and the optical fiber 37A is inserted into the fitting hole 71 of the sleeve member 61 from the proximal end side of the sleeve member 61 to bring the fluorescent body 38, the ferrule 60, and the reflective film 67 into close contact with the protective cover 36.

Then, a second bonding step of bonding the outer peripheral face of the ferrule 60 to the fitting hole 71 in order to seal the proximal end side of the fluorescent body 38 while maintaining a state where the ferrule is inserted to a position where the fluorescent body 38, the ferrule 60, and the reflective film 67 are brought into close contact with the protective cover 36. In this second bonding step, the adhesive 73 is poured and solidified between the fitting hole 71 and the outer peripheral face 60c of the ferrule 60 from the proximal end side of the sleeve member 61. Thereby, the ferrule 60 holding the fluorescent body 38 and the optical fiber 37A is received inside the sleeve member 61, and the distal end side and proximal end side of the fluorescent body 38 is sealed. Additionally, the optical fiber 37A held by the ferrule 60 protrudes from the proximal end of the sleeve member 61.

As described above, in the sleeve member 61 that covers the outer peripheries of the fluorescent body 38 and the reflective film 67, the distal end side of the fluorescent body 38 is sealed by bonding the protective cover 36 to the receiving portion 70, and the proximal end side of the fluorescent body 38 is sealed by bonding the ferrule 60 and the sleeve member 61 together. Thereby, when diagnosis is performed using an endoscope or when washing disinfection processing is performed, it is possible to prevent moisture or gas volatilized from medicine from advancing the inside of the sleeve member 51. Thus, deterioration of the fluorescent body 38 and the reflective film 67 received in the sleeve member 61 can be prevented.

Although the above first embodiment has the configuration in which the ferrule 60 as the fluorescent body 38 and the holding member is received in one sleeve member 61 and the distal end side and proximal end side of the fluorescent body 38 is sealed, the present invention is not limited thereto. As in an illumination optical unit 80 of the second embodiment shown in FIGS. 7 and 8, first and second sleeve members 81 and 82 in which a sleeve member is constituted by two parts may be used.

Figure 7:
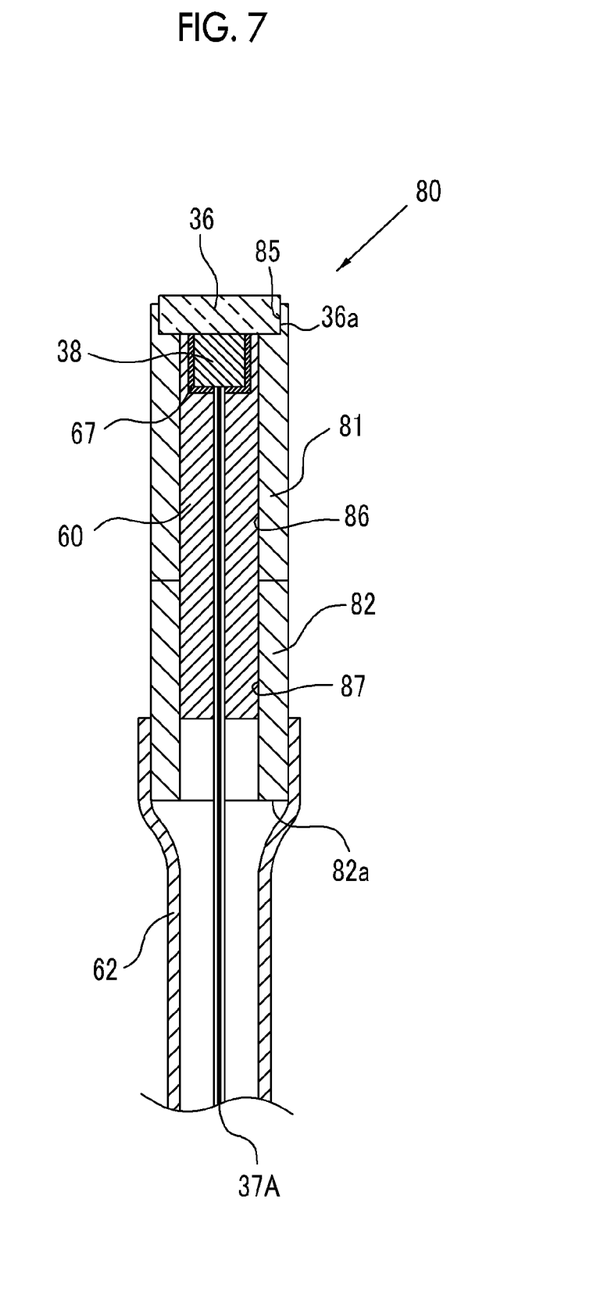
FIG. 7 is a cross-sectional view of a second embodiment in which a sleeve member is constituted by two parts.

As shown in FIG. 7, the illumination optical unit 80 includes the single mode optical fiber 37A, the fluorescent body 38, the ferrule 60, the first sleeve member 81 located on the distal end side, the second sleeve member 82 located on the proximal end side, and the protective cover 36. In addition, the same members as those of the first embodiment will be designated by the same reference numerals, and the description thereof will be omitted.

Figure 8:
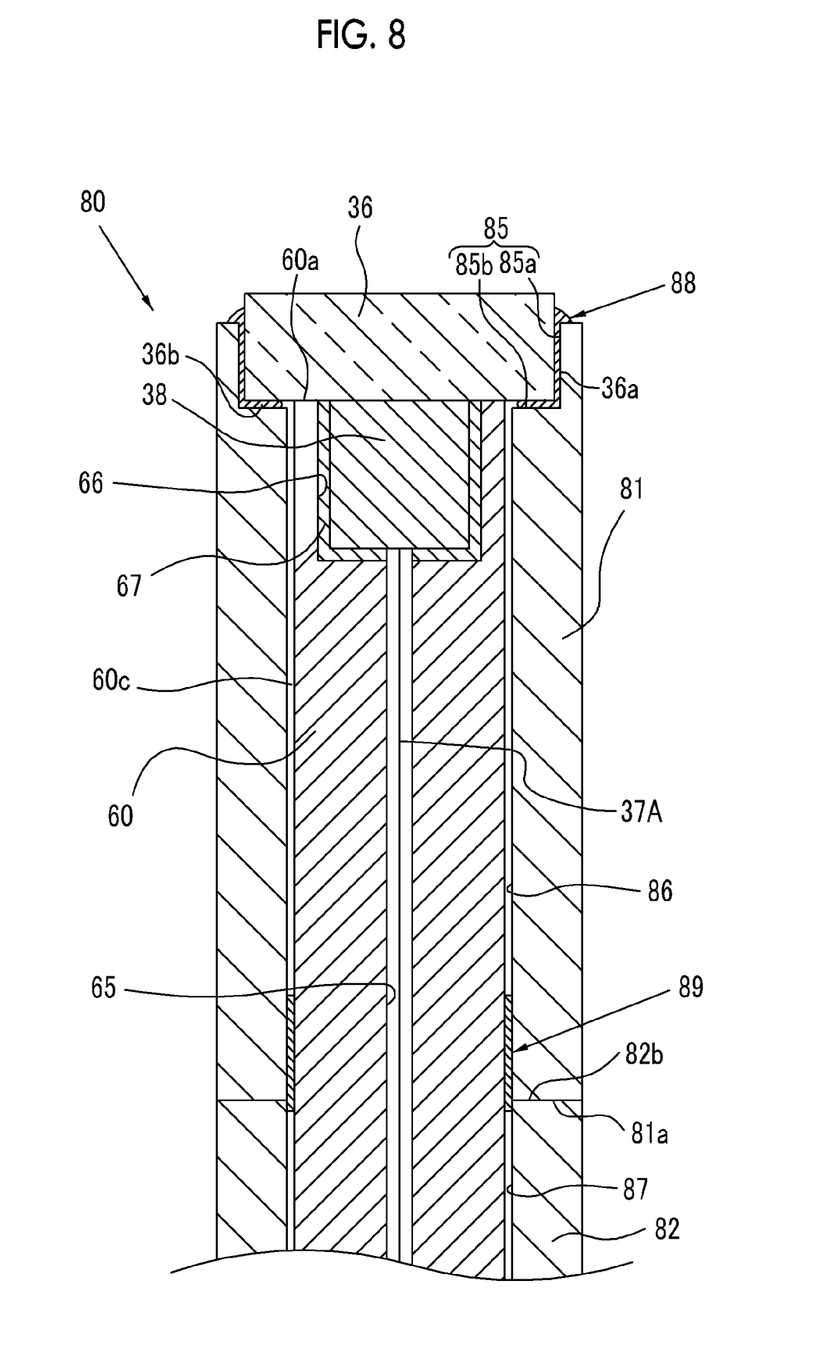
FIG. 8 is a cross-sectional view of essential parts of a second embodiment.

As shown in FIG. 8, the first sleeve member 81, similarly to the sleeve member 61 of the above first embodiment, is formed in a substantially cylindrical shape that has a receiving portion 85 that receives the protective cover 36, and a fitting hole 86 into which the outer peripheral face 60c of the ferrule 60 fits. The second sleeve member 82 has the same external diameter as the first sleeve member 81, and is formed in a substantially cylindrical shape that has a fitting hole 87 of the same internal diameter as the fitting hole 86 of the first sleeve member 81.

The axial length obtained by summing up the first and second sleeve members 81 and 82 is formed so as to be longer than the total length of the ferrule 60, and when the ferrule 60 is fitted to the fitting holes 86 and 87, the proximal end face 82a of the sleeve member 82 protrudes to the proximal end side more than the ferrule 60. Additionally, the optical fiber 37A held by the ferrule 60 protrudes to the proximal end side from the proximal end face 82a (refer to FIG. 7) of the sleeve member 82.

In a manufacturing process of manufacturing the illumination optical unit 80 of the above configuration, first, the first bonding step is performed in order to seal the distal end side of the fluorescent body 38. In this first bonding step, similarly to the bonding of the sleeve member 61 and the protective cover 36 of the above first embodiment, a predetermined amount of adhesive 88 is poured between an inner peripheral face 85a of the receiving portion 85 and the outer peripheral face 36a of the protective cover 36 to bond the protective cover 36 to a receiving portion 85. After this first bonding step, the ferrule 60 that holds the fluorescent body 38 and the optical fiber 37A is inserted into the fitting hole 86 of the first sleeve member 81 from the proximal end side of the first sleeve member 81 to bring the fluorescent body 38, the ferrule 60, and the reflective film 67 into close contact with the protective cover 36.

Then, the second bonding step is performed while maintaining a state where the ferrule is inserted to a position where the fluorescent body 38, the ferrule 60, and the reflective film 67 are brought into close contact with the protective cover 36. In this second bonding step, an adhesive 89 is poured between the fitting hole 86 and the outer peripheral face 60c of the ferrule 60 from the proximal end side of the first sleeve member 81 to bond the outer peripheral face 60c of the ferrule 60 to the fitting hole 86. In addition, the same adhesives as the adhesives 72 and 73 of the above first embodiment are used as the adhesives 88 and 89.

Moreover, a step of combining the second sleeve member 82 with the proximal end side of the first sleeve member 81 is performed after the second bonding step. In the present embodiment, as a method of combining these members, the proximal end face 81a of the first sleeve member 81 and the distal end face 82b of the second sleeve member 82 are butted against each other, and an adhesive (not shown) is poured therebetween to perform bonding.

By constituting the sleeve member by two parts as described above, in addition to the effects of the above first embodiment, the stress that the first sleeve member 81 receives from the protective tube 62 can be suppressed. That is, since the protective tube 62 is inserted through the insertion part 16 along with the optical fiber 37A, the protective tube may be pulled to the proximal end side, for example, when the bending portion 16b is bent. In the case of the above first embodiment, peeling, cracking, or the like of the adhesive may occur under any stress in the bonded portion between the sleeve member 61 and ferrule 60 that seals the proximal end side of the fluorescent body 38 because the sleeve member 61 receives stress directly from the protective tube 62 when the protective tube 62 is pulled. However, in the illumination optical unit 80 of the present embodiment, the second sleeve member 82 is interposed between the first sleeve member 81 and the protective tube 62. Therefore, the first sleeve member 81 no longer receives stress directly from the protective tube 62. As a result, the bonded portion between the first sleeve member 81 and the ferrule 60 that seals the proximal end side of the fluorescent body 38 can be prevented from being damaged.

Figure 9:
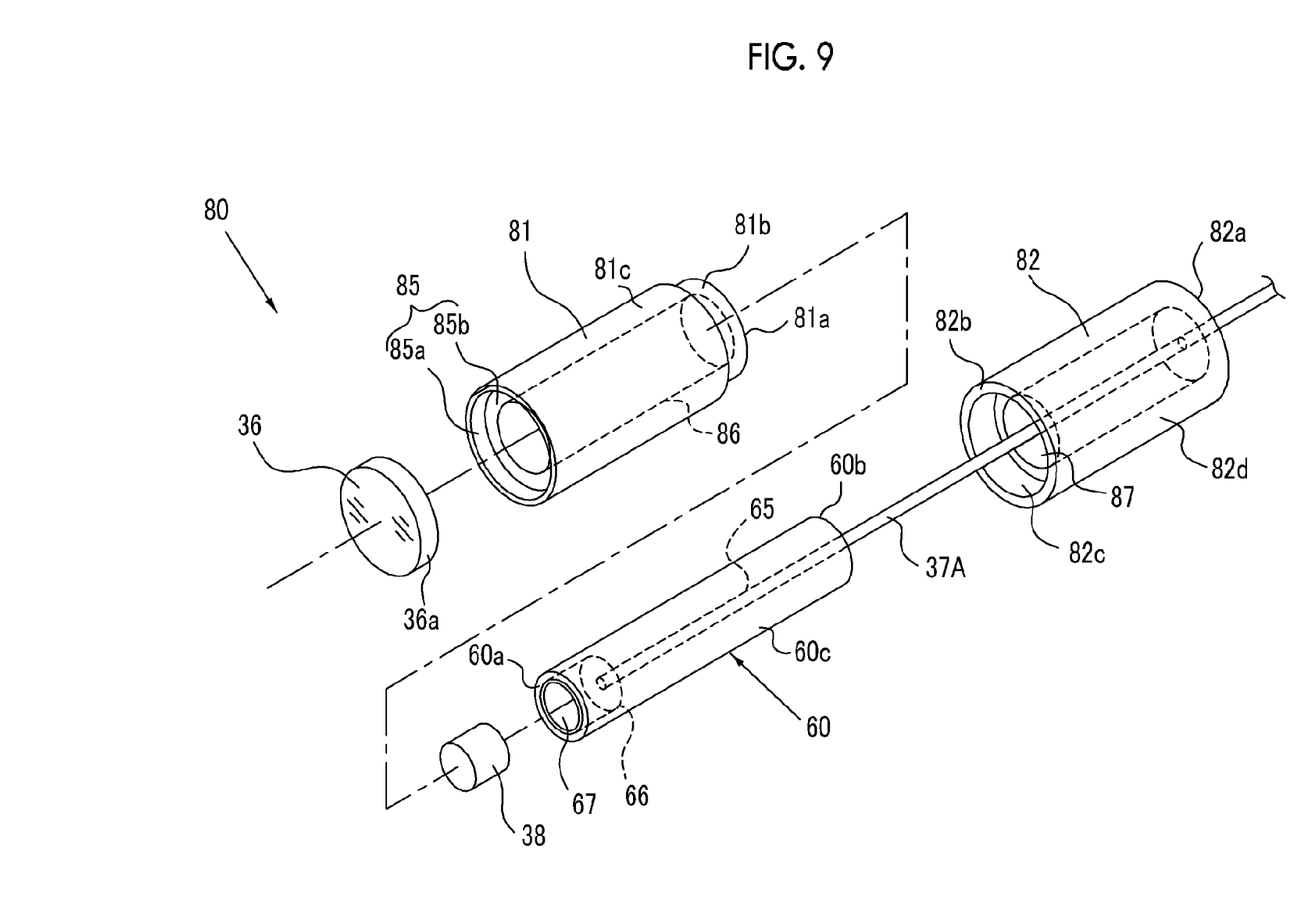
FIG. 9 is a perspective view showing a modification of the second embodiment.
Figure 10:
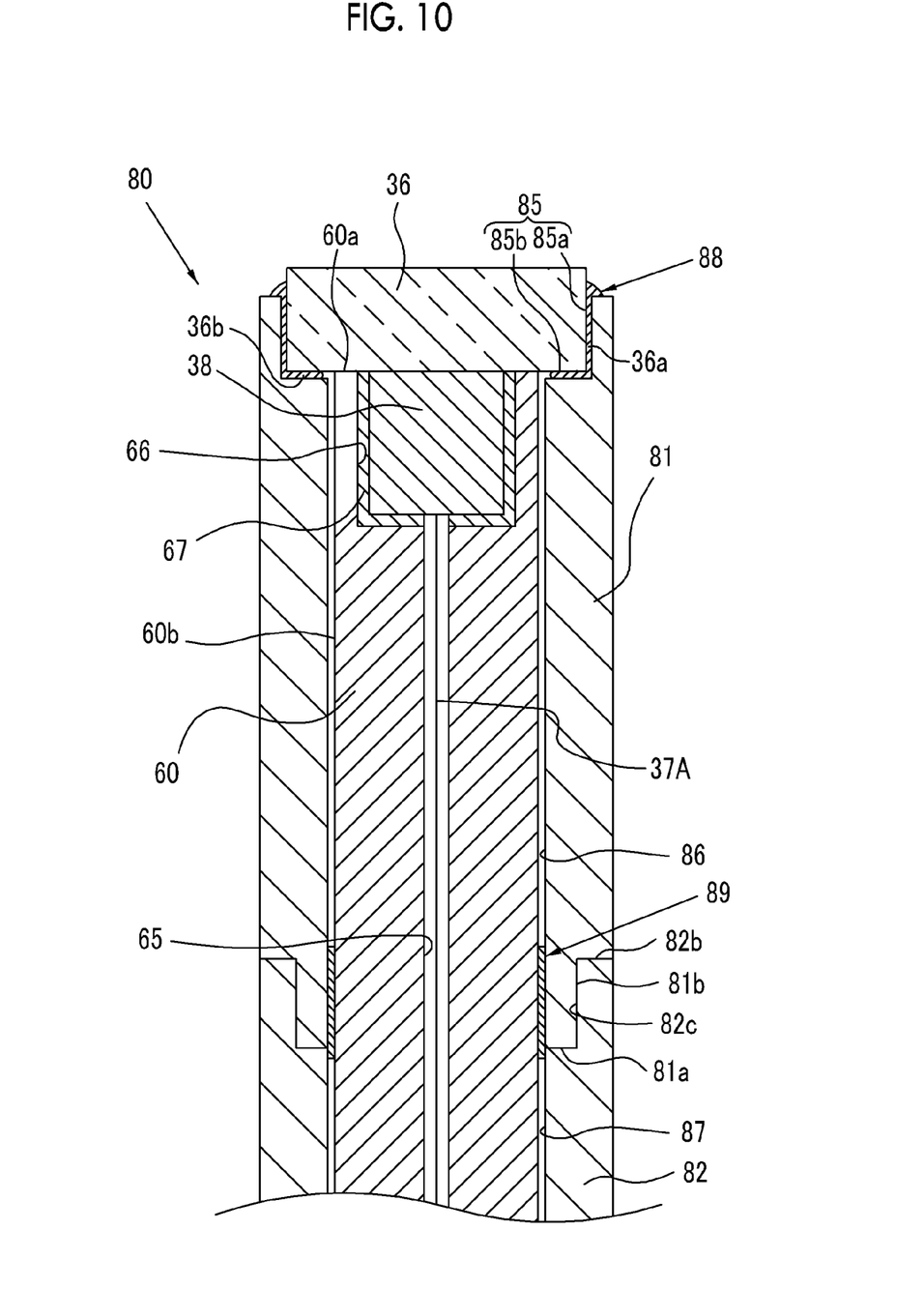
FIG. 10 is a cross-sectional view of essential parts of the example shown in FIG. 9.

In the above second embodiment, the first and second sleeve members 81 and 82 are combined together such that the mutual end faces thereof are butted against each other. However, the present invention is not limited thereto. As shown in FIGS. 9 and 10, the first and second sleeve members may be combined together such that an outer peripheral end 81b that is continuous from the proximal end face 81a of the first sleeve member 81 and an inner peripheral end 82c that is continuous from the distal end face 82b of the second sleeve member 82 are fitted to each other. In this case, the outer peripheral end 81b is formed such that the external diameter thereof is one step smaller than that of the outer peripheral face 81c of the first sleeve member 81, and the inner peripheral end 82c is formed such that the internal diameter thereof is one step larger than the fitting hole 87 of the second sleeve member 82. If the outer peripheral end 81b and the inner peripheral end 82c are fitted to each other, the outer peripheral faces 81c and 82d and the fitting holes 86 and 87 of the first and second sleeve members 81 and 82 become the same flush faces, respectively.

Additionally, the first and second sleeve members 81 and 82 may be combined together, with the fitting between the outer peripheral end 81b and the inner peripheral end 82c as tight fitting, simply by the fitting between both, or first and second sleeve members 81 and 82 may be combined together by fitting and bonding the outer peripheral end 81b and the inner peripheral end 82c to each other. In addition, in the example shown in FIGS. 9 and 10, the outer peripheral end 81b of the sleeve member 81 and the inner peripheral end 82c of the sleeve member 82 are fitted to each other. However, the inner peripheral end that is continuous from the proximal end face of the sleeve member 81 and then outer peripheral end that is continuous from the distal end side of the sleeve member 82 may be fitted to each other.

Additionally, although the electronic endoscope that observes an image obtained by imaging the state of the subject using an imaging element has been described as an example in the above embodiment, the present invention is not limited thereto, and can also be applied to an endoscope that adopts an optical image guide to observe the state of a subject. Furthermore, although the endoscope including the two illumination optical units has been described as an example in the above embodiment, the present invention is not limited thereto, and can be applied also to an endoscope including one illumination optical unit or an endoscope including three or more illumination optical units.

What is claimed is:

1. An illumination optical unit for an endoscope comprising:
    an optical fiber that guides a laser beam supplied from a laser beam source to a distal end of the optical fiber and emits the guided laser beam from the distal end;
    a fluorescent body that is excited by the laser beam emitted from the optical fiber to emit florescent light and that forms white light consisting of the fluorescent light and the laser beam;
    a holding member that holds the fluorescent body, has a fluorescent body holding portion opened on a distal end side, and a through hole that is continuous from a proximal end of the fluorescent body holding portion and allows the optical fiber to be inserted therethrough, and is formed in a substantially cylindrical shape;

a sleeve member that has an inner peripheral face fitted to an outer peripheral face of the holding member and has a distal end and a proximal end opened; and a protective cover that is held by the sleeve member, covers the distal end side of the fluorescent body, and transmits the fluorescent light and the laser beam, wherein the optical fiber is made to protrude from the proximal ends of the holding member and the sleeve member, the distal end side of the fluorescent body is sealed by bonding the sleeve member and the protective cover, and a proximal end side of the fluorescent body is sealed by bonding the sleeve member and the holding member.

2. The illumination optical unit for an endoscope according to claim 1, further comprising a protective tube that covers the optical fiber, wherein the sleeve member includes a first sleeve member that holds the protective cover and is located on a distal end side of the protective cover, and a second sleeve member combined with a proximal end side of the first sleeve member, and the protective tube is fixed to an outer peripheral face of the second sleeve member.

3. The illumination optical unit for an endoscope according to claim 2, wherein the first and second sleeve members are formed with an outer peripheral end that is continuous from one of mutually facing end faces and an inner peripheral end that is continuous from the other end face, and the outer peripheral end and the inner peripheral end fit to each other.

4. The illumination optical unit for an endoscope according to any one of claim 1, wherein the surface of the fluorescent body holding portion of the holding member is provided with a reflective film that reflects the white light emitted from the fluorescent body.

5. The illumination optical unit for an endoscope according to any one of claim 2, wherein the surface of the fluorescent body holding portion of the holding member is provided with a reflective film that reflects the white light emitted from the fluorescent body.

6. The illumination optical unit for an endoscope according to any one of claim 3, wherein the surface of the fluorescent body holding portion of the holding member is provided with a reflective film that reflects the white light emitted from the fluorescent body.

7. The illumination optical unit for an endoscope according to any one of claim 1, wherein an adhesive that bonds the sleeve member and the protective cover is a silicon-based adhesive.

8. The illumination optical unit for an endoscope according to any one of claim 2, wherein an adhesive that bonds the sleeve member and the protective cover is a silicon-based adhesive.

9. The illumination optical unit for an endoscope according to any one of claim 3, wherein an adhesive that bonds the sleeve member and the protective cover is a silicon-based adhesive.

10. The illumination optical unit for an endoscope according to any one of claim 4, wherein an adhesive that bonds the sleeve member and the protective cover is a silicon-based adhesive.

11. The illumination optical unit for an endoscope according to any one of claim 5, wherein an adhesive that bonds the sleeve member and the protective cover is a silicon-based adhesive.

12. The illumination optical unit for an endoscope according to any one of claim 6, wherein an adhesive that bonds the sleeve member and the protective cover is a silicon-based adhesive.

13. A method of manufacturing an illumination optical unit for an endoscope including an optical fiber that guides a laser beam supplied from a laser beam source to a distal end of the optical fiber and emits the guided laser beam from the distal end; a fluorescent body that is excited by the laser beam emitted from the optical fiber to emit florescent light and that forms white light consisting of the fluorescent light and the laser beam; a holding member that holds the fluorescent body, has a fluorescent body holding portion opened on a distal end side, and a through hole that is continuous from a proximal end of the fluorescent body holding portion and allows the optical fiber to be inserted therethrough, and is formed in a substantially cylindrical shape; a sleeve member that has an inner peripheral face fitted to an outer peripheral face of the holding member and has a distal end and a proximal end opened; and a protective cover that is held by the sleeve member, covers the distal end side of the fluorescent body, and transmits the fluorescent light and the laser beam, the method comprising:

bonding the sleeve member and the protective cover to seal the distal end side of the fluorescent body;

inserting the holding member holding the fluorescent body and the optical fiber into the inside of the sleeve member from a proximal end side of the sleeve member with the distal end being sealed by the protective cover, to bring the fluorescent body into close contact with the protective cover; and bonding the holding member and the sleeve member together to seal the proximal end side of the fluorescent body, in a state where the fluorescent body is brought into close contact with the protective cover, and the optical fiber is arranged on the proximal end side of the fluorescent body.

14. The method of manufacturing an illumination optical unit for an endoscope according to claim 6, wherein the sleeve member includes a first sleeve member that holds the protective cover and is located on a distal end side, and a second sleeve member combined with a proximal end side of the first sleeve member, and the step of bonding the holding member and the sleeve member together to seal the proximal end side of the fluorescent body has bonding the holding member and the first sleeve member together, and bonding a proximal end face of the first sleeve member and a distal end face of the second sleeve member together.

* * * * *